United States Patent [19]

Trowbridge

[11] Patent Number: 4,582,797

[45] Date of Patent: Apr. 15, 1986

[54] MONOCLONAL ANTIBODIES SPECIFIC FOR HUMAN HEMATOPOIETIC CELL SURFACE GLYCOPROTEINS

[75] Inventor: Ian S. Trowbridge, San Diego, Calif.

[73] Assignee: The Salk Institute for Biological Studies, San Diego, Calif.

[21] Appl. No.: 470,586

[22] Filed: Feb. 28, 1983

Related U.S. Application Data

[63] Continuation-in-part of Ser. No. 190,728, Sep. 25, 1980, abandoned.

[51] Int. Cl.[4] ................. C12N 5/00; C12N 15/00
[52] U.S. Cl. ........................... 435/68; 435/41; 435/172.2; 435/240; 435/241; 935/101; 935/103
[58] Field of Search ............. 435/240, 241, 172.2, 435/41, 68, 172.2; 935/101, 103

[56] References Cited

U.S. PATENT DOCUMENTS

| | | | |
|---|---|---|---|
| 4,172,124 | 10/1979 | Koprowski | 424/85 |
| 4,196,265 | 4/1980 | Koprowski | 435/2 |
| 4,271,145 | 6/1980 | Wands | 424/85 |
| 4,361,549 | 11/1982 | Kung | 435/172.2 X |
| 4,363,799 | 12/1982 | Kung | 435/172.2 X |
| 4,364,933 | 12/1982 | Kung | 435/172.2 X |
| 4,364,935 | 12/1982 | Kung | 435/172.2 X |
| 4,364,936 | 12/1982 | Kung | 435/172.2 X |
| 4,364,937 | 12/1982 | Kung | 435/172.2 X |

OTHER PUBLICATIONS

Kohler, C. et al., Eur. J. Immunol., 6, 511-519, (1976).
Melchers, F. et al., Second Workshop on "Functional Properties of Tumors of T and B Lymphocytes", Apr. 3-5, 1978, Bethesda, Md., pp. IX-XIX.
Trowbridge, I. S., "Interspecies Spleen-Myeloma Hybrid Producing Monoclonal Antibodies . . . ", J. Exp. Med., 1978, 313-323.
Borowitz, M. J. et al., Human Pathology, 15 (10), 928-934, (Oct. 1984).

*Primary Examiner*—Sidney Marantz
*Attorney, Agent, or Firm*—Fitch, Even, Tabin & Flannery

[57] ABSTRACT

Monoclonal antibodies are produced for a family of glycoproteins which are selectively expressed on the surface of nucleated human hematopoietic cells but which are absent from other normal human cells. Mice are inoculated with human hematopoietic cells or fragments thereof, and spleen cells obtained from the mice are fused with murine myeloma cells to produce hybridomas. The hybridomas are cultured as clones, and antibodies obtained from the individual clones are tested for their specificity for surface glycoproteins of nucleated human hematopoietic cells. Antibodies can be obtained from the culture growth medium or from ascitic fluid of mice bearing the hybridoma tumor and can be used to distinguish lymphomas from carcinomas.

9 Claims, No Drawings

MONOCLONAL ANTIBODIES SPECIFIC FOR HUMAN HEMATOPOIETIC CELL SURFACE GLYCOPROTEINS

This application is a continuation-in-part of my earlier application Ser. No. 190,728, filed Sept. 25, 1980, now abandoned.

The present invention is directed to hybridoma cell lines which produce monoclonal antibodies and more particularly to monoclonal antibodies specific for glycoproteins widely distributed in human hematopoietic cells.

BACKGROUND OF THE INVENTION

Antibodies have long been used in medical diagnosis, e.g., determining blood types, and in biological experimentation. The usefulness of antibodies, however, has been somewhat limited, as their complexity and diversity have made it very difficult to obtain homogeneous antibodies. Antibodies are complex protein or protein-based molecules which are produced by the immune systems of animals to protect the animal against foreign substances. Antibodies for medical use are generally obtained by injecting an animal with a foreign substance which will stimulate the animal's immune system and, most commonly, isolating an antibody fraction from the peripheral blood serum or from the ascitic fluid. The antibody fraction contains antibodies specific to the injected foreign substance as well as various other antibodies produced by the animal, and by known techniques, it may be possible to substantially isolate an antibody specific to the particular foreign substance. However, even when an antibody for a particular foreign substance is isolated, such antibody is actually a mixture of several antibodies which recognize various antigenic determinants of the foreign substance or related substances. While some individual antibody molecules may be highly specific, recognizing only a certain foreign substance or portion thereof, other antibody molecules may be less selective, recognizing not only the subject foreign substance but other substances as well. Because it is generally practically impossible to separate all related antibodies, even the most carefully purified antibody fractions may react with more than one substance.

In recent years, techniques of producing monoclonal antibodies have been developed which make it possible to obtain homogenous, highly specific antibodies. Generally, such antibodies are produced by immunizing an animal with a protein fraction or other foreign substance, obtaining antibody-producing cells from the animal, and fusing the antibody-producing cells with strains of myeloma cells, e.g., tumor cells, to produce hybridomas which are isolated and cultured as monoclones. The monoclonal hybridomas may either be cultured in vitro or may be grown as tumors in a host animal. Because each antibody-producing cell produces a single unique antibody, the monoclonal cultures of hybridomas each produce a homogeneous antibody which may be obtained either from the culture medium of hybridoma cultures grown in vitro or from the cells, ascitic fluid, or serum of a tumor-bearing host animal.

Not all of the hybridoma clones which result from fusing neoplastic cells with antibody-producing cells are specific for the desired foreign substance or antigen (a substance with which the antibody reacts) because many of the hybridomas will make antibodies which the inoculated animal has produced to react with other foreign substances. Even antibodies against the subject antigen will differ from clone to clone because antibodies produced by different cells may react with different antigenic determinants of the same molecule. From each clone, therefore, it is necessary to obtain the resulting antibody or the antibody-containing medium, serum or ascitic fluid and test its reactivity with the subject antigen and to test its specificity by determining with what other substances, if any, it recognizes. While the necessity of characterizing the antibody of each clone adds to the complexity of producing monoclonal antibodies, the wide variety of homogeneous antibodies which may be obtained gives investigators a number of very precise tools to map the structure and development of somatic cells.

The availability of homogeneous, highly specific monoclonal antibodies dramatically increases the value of antibodies as a diagnostic, experimental and therapeutic tool. Use of monoclonal antibodies for tumor and virus detection has been described in U.S. Pat. Nos. 4,172,124 and 4,196,265.

Monoclonal antibodies are particularly suitable for studying the pathways and processes by which cells differentiate into different types of cells. The proteins and other macromolecules in cells which may be precisely detected by monoclonal antibodies may serve as important clues to the derivation of cell lines. This may be particularly important when undifferentiated cancer cells are detected in the body and where the treatment of the cancer is dependent on the type of tumor present. The morphology of undifferentiated lymphoma cells may closely resemble the morphology of carcinoma cells, but the accepted treatments of lymphomas and carcinomas differ substantially. Thus it is highly important that it be determined as quickly as possible whether a cancer cell line in a patient is a carcinoma or a lymphoma line. Where the identity of the tumor line is not apparent from its gross morphology, highly specific monoclonal antibodies may be used to classify cell lines by their molecular composition.

SUMMARY OF THE INVENTION

Monoclonal antibodies are produced which are specific for cell surface glycoproteins, which are widely distributed on human hematopoietic cells, particularly human B and T lymphocytes lines, and which are generally absent from non-hematopoietic cells. Mice are inoculated with a line of human lymphocytes, and spleen cells or lymph node cells are obtained from the inoculated mice and fused with mice tumor cells. Monocultures of the fused cells are produced, and the antibodies obtained from the monoclones are tested for their reactivity with cell surface glycoproteins particular to nucleated hematopoietic cells to select the monoclones which produce antibodies reactive with the glycoproteins. The monoclonal antibodies may be particularly useful to distinguish undifferentiated carcinomas from undifferentiated lymphomas.

DETAILED DESCRIPTION OF THE PREFERRED EMBODIMENTS

Monoclonal antibodies are produced which are specific for a family of glycoproteins which have been designated T29/33 and which are widely distributed on the surface of human nucleated hematopoietic cells but which are absent from other human tissue cells. T29/33 glycoproteins are expressed on more than 95% of peripheral blood leukocytes, and a similar broad distribution is found in other lymphoid and hematopoietic tissues, including spleen, thymus, bone marrow and tonsil. They do not appear in detectable amounts in erythrocytes, liver, brain or kidney tissue, nor a variety of other normal adult human tissues. T29/33 glycoproteins have been characterized as having molecular weights of between about 200,000 and about 220,000 as determined by their migration on SDS-polyacrylamide gel.

Similar hematopoietic cell surface glycoproteins are known in non-human species. A family of mouse glycoproteins designated T-200 has been identified, Trowbridge *J. Exp. Med.* 148:313, (1978). T-200 glycoproteins obtained from mouse cell lines ASL1 and BW5147, Hyman et al. *Cold Spring Harbor Symp. Quant. Biol.* 41:407 (1976), have been proteolysed and peptide mapped using techniques described in Omary et al. *J. Biol. Chem.* 255:1662 (1980).

Lymphocytes are introduced into animals, to induce the production of antibodies reactive with proteins and glycoproteins, inluding T29/33 glycoproteins found on the cell surface of most nucleated hematopoietic cells. The animal chosen for inoculation is not critical, but it is preferred that the strain of animal be well characterized. Because various strains of murines, i.e., rats, mice, etc., are well characterized, and since various murine-derived neoplastic cells are also available as well-characterized cultures, mice are chosen for production of the antibodies herein described, although it is to be understood that the invention is not limited to murine-derived monoclonal antibodies.

BALB/c mice are inoculated intraperitoneally with $2 \times 10^7$ cells from the normal human T leukemic line CCRF-CEM, Foley et al. *Cancer* 18 522, (1965), suspended in standard tissue culture media. After 2 weeks, the mice are inoculated with a booster of at least $10^6$ cells. Four days after the second inoculation, the mice are sacrificed and their spleens are taken. A spleen cell suspension is prepared in the manner taught by Gerhard et al., *Eur. J. Immunol* 5, 720–725 (1975). The red blood cells are removed by lysing in 0.83% $NH_4Cl$ for 15 minutes at 4° C., and the resulting cell suspension is washed by one centrifugation ($800 \times g$) in heat-inactivated horse serum and one centrifugation in protein-free Dulbecco's modified Eagles medium.

Because the antibody-producing cells obtained from the spleen do not independently reproduce, and thus cannot be cultured, they are fused with cells which may be independently cultured either in vivo or in vitro so that the genetic and metabolic processes of the fused hybridomas have characteristics of each of the parent cells, and it is intended that certain of the cells obtained will have the capabilities to independently reproduce and to produce the antibody of the antibody-producing parent cell. Some tumor cells, particularly myeloma cells, may be advantageously fused with antibody-producing cells to provide viable antibody-producing cultures of hybridomas. Although it is not necessary, it is preferred that the tumor cells and antibody-producing cells be derived from the same species to enhance the likelihood that the genetic and biochemical properties of the parent cells will be compatible and thus produce viable hybridomas. A number of myeloma cultures have been characterized, and herein, the mice-derived non-antibody producing myeloma cell line S194/5.XX0.BU.1, Trowbridge, *J. Exp. Med.*, 148, 313–323 (1978), samples of which are on deposit at the American Type Culture Collection, are used to produce the hybridomas. It is to be understood that other tumor lines, which include but are not limited to P3, Y3, SP2/0, MPC-11 and their derivatives, may also be used. It is advantageous to select a myeloma line which does not produce an antibody so that the resulting hybrid will only produce antibody chains of the parent spleen or lymph node cell.

The myeloma cells are maintained in Dulbecco's modified Eagle's medium supplemented with 10% horse serum. $10^7$ myeloma and $10^8$ cells obtained from the mice immunized with CCRF-CEM, are resuspended for fusion in a 40% solution (v/v) of a fusion promoter, such as polyetheylene glycol 1500, according to the methods of Trowbridge supra. Cell hybrids are selected in hypoxanthine-aminopterin-thymidine (HAT) medium, all growth in HAT medium being indicative of successful hybridization of mouse spleen and mouse myeloma cells, for unfused myeloma cells fail to grow therein. Their production of antibodies against the lymphocytes used to inoculate the mice is tested by the antibody-binding assay described by Williams et al., *Cell* 12, 663 (1977). Hybrid cells are cloned by the method of limiting dilution in Falcon microtiter plates.

Clones of hybridomas may be grown in vitro according to known tissue culture techniques, such as is described by Cotton et al., *Eur. J. Immunol.* 3, 136 (1973). Alternatively, hybridomas may be grown in vivo as tumors in a histocompatible animal or in athymic nude mice. The antibodies may be recovered from the in vitro culture medium or supernatant or from the serum or ascitic fluid of the animal by means known in the art, e.g., Gerhard et al., *Proc. Natl. Acad. Sci.*, 75, pp. 1510–1514 (1978). In some cases, it may be advantageous to obtain the antibodies directly from the cells of the culture or tumor.

The specificity of the antibody from each clone for nucleated hematopoietic cells is examined by the methods of Williams supra., and clones which produce antibody specific for nucleated hematopoietic cells are selected. When a useful hybridoma clone is produced, it is generally advantageous to reclone the cell line to avoid overgrowth of cultures with variant cells no longer producing antibody. Because the hybridoma contains some, but not all, of the genetic material of each parent cell, the full characteristics of the hybridoma are not known. Often a hybridoma clone, due to original genetic deficiency or subsequent chromosome loss, after several passages may lose its ability to reproduce and/or to produce the particular antibody. Accordingly, it is important, soon after the initial hybridization, that a hybridoma clone of interest is recloned to ensure the availability of functioning strains of the antibody-producing hybridoma.

EXAMPLE

Hybridoma cell lines are produced by mixing $10^8$ spleen cells obtained from BALB/c mice immunized with CCRF-CEM hematopoietic cells with $10^7$ S194/5.XX0BU.1 cells. The cell mixture is centrifuged at $800 \times g$, and the cells are resuspended for fusion in a 40% (v/v) solution of polyethylene glycol 1500 in modified Eagle's medium. Cell hybridomas are selected in HAT medium and cloned by the method of limiting dilution in microtiter plates. The culture media of the resulting monoclones are tested for immuno activity against hematopoietic cell lines and other human cell lines. Hybridoma cell lines are chosen for further culturing whose media exhibits immuno response to human hematopoietic cell lines and no immuno response to other human cell lines. Monoclonal antibody fractions are obtained from the culture media of the selected hybridomas.

A monoclonal hybridoma cell line is produced and selected which produces a monoclonal antibody which reacts with the T29/33 glycoproteins in nucleated hematopoietic cells but does not react with other normal human cells, including erythrocytes, liver, brain or kidney tissue. Because the cell line produces a monoclonal antibody specific for T29/33 glycoproteins, the monoclonal antibody produced thereby has also been designated T29/33. The hybridoma cell line is on deposit at the American Type Culture Collection of 12301 Parklawn Drive, Rockville, Md., under accession number ATCC CRL 8036. Reclones of the ATCC CRL 8036 cell line also produce T29/33 monoclonal antibody.

The reactivity of the T29/33 monoclonal antibody with glycoproteins found on the surface of nucleated hematopoietic cells is further demonstrated by the molecular weight determination of the glycoproteins obtained by monoclonal antibody immunoprecipitation of hematopoietic cell lysates, Trowbridge et al., *Eur. J. Immunol.* 6:777, 1976. Lysates of $^{125}$I-labled CCRF-HSB2, a T-cell Lymphocytic leukemia cell line, Adams et al. *Exp. Cell Res.* 62:5 (1970), and CCRF-SB, a normal B-lymphocyte line, Foley et al. *Cancer* 18:522 (1965), are each precipitated with T29/33 monoclonal antibody. The precipitated glycoproteins from each cell line are electrophoresed on sodium dodecyl sulfate polyacrylamide gel, and two different molecular weight precipitates are obtained. The molecular weight of the T-cell T29/33 glycoprotein is about 200,000, and the molecular weight of the B-cell T29/33 glycoprotein is about 220,000. Both probably correspond to the high molecular weight glycoproteins in normal human T and B lymphocytes earlier reported, Andersson et al. *Int. J. Cancer* 17:40 (1976).

Further evidence of the hematopoietic cell specificity of T29/33 monoclonal antibody is the high degree of homology of the human glycoproteins with which the antibody reacts and mouse T200 hematopoietic cell surface glycoprotein. Human T leukemia cell lines CCRF-CEM and CCRF-HSB2 are both metabolically labeled with L-[$^{35}$S] methionine, immunoprecipitated with T29/33 monoclonal antibody and proteolysed, Omary supra. Comparison of peptide maps produced from T200 ASL1 mouse cell glycoprotein proteolysates and T29/33 human T-cell glycoprotein proteolysates indicate that 17 labled peptides of respective proteolysates are shared by the mouse and human glycoproteins, 15 peptides are unique to the mouse glycoprotein and 13 peptides are unique to the human glycoprotein.

Because T29/33 monoclonal antibody is generally reactive with hematopoietic cells and is nonreactive with other tissues, it serves as an important diagnostic tool in tumor biopsy for classifying cancer cell lines. The presence of T29/33 glycoproteins in a nonclassified cancer cell line, as determined by immunoprecipitation, radioimmunoassay, autoradiography, immunofluorescence or other known immuno techniques utilizing T29/33 monolonal antibody, is a strong indication that the cancer cell line is a lymphoma rather than a carcinoma.

Modifications obvious to one with ordinary skill in the art may be made without departing from the scope of the present invention. For example, antibody production may be induced in the host animal by inoculating the animal with other human hematopoietic cell lines containing a T29/33 glycoprotein or with cell membrane fragments or cell-membrane-derived material rather than with complete hematopoietic cells.

Various features of the invention are set forth in the following claims.

What is claimed is:

1. A mouse monoclonal antibody produced by a hybridoma formed by fusion of cells from a mouse myeloma line and either spleen cells or lymph node cells from a mouse previously immunized with human hematopoietic cells, which antibody reacts with specific hematopoietic cell surface glycoproteins that react with monoclonal antibody produced by cell line ATCC CRL 8036, which glycoproteins are present in essentially all human nucleated hematopoietic cells, but said monoclonal antibody does not react with other normal human tissue cells.

2. The monoclonal antibody of claim 1 which is produced from a hybridoma formed by the fusion of S194/5.XX0.BU.1 myeloma cells and cells from a mouse previously immunized with CCRF-CEM human T leukemic cells.

3. The method of preparing monoclonal antibodies which react with essentially all nucleated hematopoietic cells but do not react with other normal human tissue cells, which method comprises either culturing in vitro or injecting into a histocompatible animal the hybridoma ATCC CRL 8036 and recovering the antibodies.

4. A method in accordance with claim 3 wherein said hybridoma is injected into athymic nude mice and recovering the antibodies from ascitic fluid therefrom.

5. A monoclonal antibody which reacts with specific hematopoietic cell surface glycoproteins that react with monoclonal antibody produced by cell line ATCC CRL 8036, which glycoproteins are present in essentially all human nucleated hematopoietic cells, but said antibody does not react with other normal human tissue cells, the monoclonal antibody prepared by the method comprising the steps of:
    (a) immunizing mice with human hematopoietic cell;
    (b) removing the spleens from said mice and making a suspension of the spleen cells;
    (c) fusing said spleen cells with mouse myeloma cells in the presence of a fusion promoter;
    (d) diluting and separately culturing the fused cells in a medium which will only support growth of fused myeloma cells;
    (e) examining the medium from each of the separate cultures containing a hybridoma for the presence of antibodies which react with human hematopoietic cells;
    (f) selecting and cloning a hybridoma producing a monoclonal antibody which reacts with cell surface glycoproteins particular to all human nucleated hematopoietic cells, and specifically with said cell surface glycoproteins, but not with cell surface glycoproteins from other normal tissue cells; and
    (g) recovering said monoclonal antibody.

6. The monoclonal antibody of claim 5 which is prepared by injecting said hybridoma clones intraperitoneally into a histocompatible animal and recovering said antibody from ascitic fluid of the animal.

7. The monoclonal antibody of claim 5 prepared by the method wherein BALB/c mice are immunized with CCRF-CEM normal human T leukemic cells.

8. The monoclonal antibody of claim 7 prepared by the method wherein said spleen cells are fused with SI94/5.XX0.BU.1 mouse myeloma cells.

9. The monoclonal antibody according to claim 5 produced by the cell line ATCC CRL 8036.

* * * * *

UNITED STATES PATENT AND TRADEMARK OFFICE
CERTIFICATE OF CORRECTION

PATENT NO. : 4,582,797
DATED : April 15, 1986
INVENTOR(S) : Trowbridge, Ian S.

It is certified that error appears in the above-indentified patent and that said Letters Patent is hereby corrected as shown below:

Column 1, line 6 insert:
This invention was made with Government support under Grant Number CA-17733 awarded by the National Institutes of Health. The Government has certain rights in this invention.

Signed and Sealed this

Sixth Day of December, 1994

Attest:

BRUCE LEHMAN

Attesting Officer          Commissioner of Patents and Trademarks